United States Patent [19]

Ranke et al.

[11] Patent Number: 4,713,940
[45] Date of Patent: Dec. 22, 1987

[54] PROCESS FOR OBTAINING $C_{2+}$ OR $C_{3+}$ HYDROCARBONS FROM GASEOUS MIXTURES

[75] Inventors: Gerhard Ranke, Poecking; Friedrich Siegert, Wolfratshausen, both of Fed. Rep. of Germany

[73] Assignee: Linde Aktiengesellschaft, Wiesbaden, Fed. Rep. of Germany

[21] Appl. No.: 927,986

[22] Filed: Nov. 7, 1986

[30] Foreign Application Priority Data

Nov. 7, 1985 [DE] Fed. Rep. of Germany ....... 3539554

[51] Int. Cl.[4] .............................................. F25J 3/00
[52] U.S. Cl. ................................................. 62/17; 55/68; 62/20
[58] Field of Search .................. 62/17, 20; 55/44, 51, 55/68

[56] References Cited

U.S. PATENT DOCUMENTS

| | | | |
|---|---|---|---|
| 2,757,754 | 8/1956 | Natta | 55/44 |
| 3,633,371 | 1/1972 | Davison | 62/17 |
| 3,899,312 | 8/1975 | Kruis et al. | 62/17 |
| 4,038,332 | 7/1977 | Carter | 62/17 |
| 4,383,842 | 5/1983 | O'Brien | 62/20 |
| 4,451,274 | 5/1984 | O'Brien | 62/17 |
| 4,533,373 | 8/1985 | Butz et al. | 62/17 |
| 4,563,202 | 1/1986 | Yao et al. | 62/17 |
| 4,609,389 | 2/1986 | Karwat | 62/17 |
| 4,617,038 | 10/1986 | Mehra | 62/17 |

Primary Examiner—Ronald C. Capossela
Attorney, Agent, or Firm—Millen & White

[57] ABSTRACT

A process is disclosed for obtaining $C_{2+}$ or $C_{3+}$ hydrocarbons from hydrocarbon-containing gaseous mixtures by pressure scrubbing with a physically acting solvent selective for $C_{2+}$ and, respectively, $C_{3+}$ hydrocarbons. The solvent, after loading, is regenerated and reused. In order to avoid impurities in the $C_{2+}$ and, respectively, $C_{3+}$ product in an economical and energy-saving way, the loaded solvent is subjected to expansion to a pressure lying below the critical pressure of the solvent-gas mixture, and to heating and partial evaporation in order to drive off concomitantly dissolved inert gases. The solvent, reduced in its content of inert gases, is then to be passed on to regeneration. The process is advantageous, in particular, in cases where crude gases are to be processed which exhibit a low concentration of components to be scrubbed out.

13 Claims, 2 Drawing Figures

PROCESS FOR OBTAINING $C_{2+}$ OR $C_{3+}$ HYDROCARBONS FROM GASEOUS MIXTURES

BACKGROUND OF THE INVENTION

The invention relates to a process for obtaining $C_{2+}$ or $C_{3+}$ hydrocarbons from gaseous mixtures that contain hydrocarbons, by pressure scrubbing with a physical solvent selective for $C_{2+}$ and, respectively, $C_{3+}$ hydrocarbons, the resultant loaded solvent being then regenerated and reused.

It is known from DAS No. 1,114,475 to use a physical scrubbing step for removing a readily soluble component from a gaseous mixture with the aid of a selective solvent in such a way that this component is scrubbed out in the upper portion of the scrubbing column and, in the same column, in the lower section, an inert gas is employed for stripping from the solvent, other components having a lower solubility than the desired gas component dissolved in the solvent. The inert gas employed as the stripping gas in this process shows no solubility, or is only sparingly soluble, in the solvent utilized. A special feature of the scrubbing step in the conventional process resides in that a portion of desired component is added to the stripping gas in order to avoid partial stripping off of the desired component from the solvent.

Stripping of more sparingly soluble components from a loaded scrubbing fluid with an inert gas is possible if either the gas component which is to be dissolved in the solvent has such a high solubility that any amount of inert gas simultaneously dissolved in the solvent is negligible, because the dissolved gas does not need to meet high purity requirements with regard to the inert gas employed, or the inert gas may permissively be a constituent of the remaining, scrubbed gas.

According to one embodiment of DAS No. 1,114,475, a butadiene-butene gas mixture is scrubbed with a solvent wherein butadiene is readily soluble in the chosen solvent. Nitrogen is used as the inert gas and the solvent employed is dimethylformamide (DMF). In accordance with the solubility data in Landoldt Boernstein, volume "Technik" [Technology] 4th part, issue C, 1976, pages 268, 276, 277, the following solubilities apply for these gases in DMF at 20° C. and under a partial pressure of 0.1 bar:

Butadiene: $=39$ $Nm^3/t$ bar
Butene: $=19$ $Nm^3/t$ bar
Nitrogen: $=0.058$ $Nm^3/t$ bar The resultant solubility ratio of butadiene:nitrogen $=39:0.058=672$. On the basis of this ratio, the influence of the dissolved nitrogen on the purity of butadiene, obtained as the product, can be ignored.

The relationships are different in the production of heavy hydrocarbons, for example $C_{2+}$ hydrocarbons, from natural gas or other gaseous mixtures subjected to scrubbing with an organic solvent, as described, for example, in U.S. Pat. No. 4,526,594. If, for example, $C_{2+}$ is to be obtained from natural gas in such a system the methane content in the product $C_{2+}$ must lie below 1 vol-%. Normally, only methane is contained in natural gas as the lighter component.

Stripping off the methane dissolved in the solvent after the scrubbing step with the aid of an inert gas, such as nitrogen, is not possible since extremely strict calorific value conditions must be met by the head product from the scrubbing step. Consequently, dilution of methane with nitrogen is not permissible. Therefore, in the case of obtaining $C_{2+}$ by means of a physical scrubbing operation, the principle of stripping off other components from a solvent containing dissolved product gas, as described in DAS No. 1,114,475, cannot be applied.

It is also known to strip off poorly soluble components with product gas in a combined scrubbing-stripping column, the stripping gas being generated by heating the loaded solvent. Such a method is disclosed, for example, in DOS No. 3,247,773. The loaded solvent is heated under pressure and the thus-released gas is recycled into the scrubbing column. During this step, at least part of the lesser soluble $CO_2$, which is dissolved along with $H_2S$, is stripped off.

The mode of operation of stripping off more sparingly soluble components from a loaded scrubbing liquid is, however, only possible under pressures lying below the critical pressure of the scrubber bottom liquid. In the case of a $CO_2/H_2S$ mixture, the critical pressure is very high, normally above 73 bar, so that in this case no drastic limitations arise. However, in the case of a hydrocarbon mixture, such as those which usually occur in natural gases, the critical pressure is in the range of from about 30 to 45 bar. Accordingly, the conventional stripping methods operating under pressure can be utilized only with great limitations, inasmuch as the customary pressures for natural gases fed into a pipeline system are in a range of 70 bar.

Based on this restriction of the pressure range, processes, such as the one set forth in U.S. Pat. No. 4,526,594, for obtaining heavy hydrocarbons from natural gas by a physical scrubbing step recommend expanding the loaded solvent and then compressing the thus-liberated gases to such an extent that they can be fractionated in a demethanizer or deethanizer to the required product purity. However, separation by distillation, due to the expenditure in apparatus, is extremely cost-intensive and also disadvantageous from an energy standpoint since the liberated gas is obtained without being pressurized and therefore must be compressed.

SUMMARY OF THE INVENTION

It is an object of this invention to provide a process for obtaining $C_{2+}$ or $C_{3+}$ hydrocarbons from natural gas wherein the presence of impurities in the $C_{2+}$ and, respectively, $C_{3+}$ product is substantially avoided in a simple, economical, and energy-saving way.

Upon further study of the specification and appended claims, further objects and advantages of this invention will become apparent to those skilled in the art.

These objects are attained according to this invention by expanding of a loaded or enriched solvent from a $C_{2+}$ or $C_{3+}$ scrubbing column to a pressure lying below the critical pressure of the solvent-gas mixture, i.e., the loaded solvent, and heating and partially evaporating the solvent to drive off concomitantly dissolved inert gases, and passing resultant solvent, reduced in its concentration of inert gases, on to regeneration. Usually the following components are contained as inert gas in natural gas: $N_2$, CO, $CH_4$ and possibly He. In the case of $C_{3+}$-production there will also be $C_2H_6$, because this is not as soluble as $C_{3+}$. When treating technical gas mixtures, i.e. refinery-waste-gas, $H_2$, Ar and $C_2H_4$ will also be present as less soluble components.

Separation of light components or, respectively, inert gases by stripping is a mode of operation which can be performed more simply, from an economy viewpoint, than distillatory separation. Moreover, an advantage of the process of this invention is that the loaded solvent withdrawn from the bottom of the scrubbing column is at a temperature which is its boiling point at a low pressure so that the sump temperature can be kept lower and, consequently, the energy required for the stripping step can be made available at a lower temperature level, and thus at a lower expense. For example, the loaded solvent can be removed from the bottom of the scrubbing column at a temperature of about 253 to 313 K. (which is its boiling point temperature at a pressure of about 45 to 120 bar and which is limited by the used refrigerating agent), expanded to a pressure of 25 bar (which is about 20 bar below its critical pressure) and then heated up to the boiling temperature of the solvent, which is selective for $C_{2+}$ at these conditions.

The process of this invention offers a special advantage when processing crude gases having a low concentration of components to be scrubbed out. Since, as is known, the amount of solvent used in physical gas scrubbing operations is proportional to the total amount of gas to be scrubbed, a very low loading of the solvent in the bottom of the scrubbing column is obtained in these cases. For this reason, the temperature of the loaded solvent must be greatly raised in order to be at its boiling point at the crude gas pressure of the scrubbing column. This need for a great rise in temperature is eliminated by stripping off the lighter components from the loaded solvent under lower pressures in accordance with the present invention. In this connection, the loaded solvent is expanded to a pressure set at a value lying at least 5 bar below the critical pressure of the loaded solvent.

According to a further development of the process of this invention, a provision is made so that the gaseous fraction released from the loaded solvent during the expansion and subsequent heating is compressed to the crude gas pressure and recycled to the scrubbing stage. This offers the advantage that, besides methane or ethane liberated during expansion, any $C_{2+}$ and, respectively, $C_{3+}$ hydrocarbons also liberated during expansion of the loaded solvent, in accordance with the equilibrium with respect to the loaded solvent, are again scrubbed out in the scrubbing stage and consequently, a high yield of products is made possible.

Alternatively, there is also the possibility of subjecting the gaseous fraction, released from the loaded solvent during expansion and subsequent heating in the stripping stage, to a secondary scrubbing step for the recovery of $C_{2+}$ and, respectively, $C_{3+}$, hydrocarbons that have been concomitantly removed from the loaded solvent. In installations for processing of natural gas, it is frequently necessary to combust a specific amount of gas for driving compressors in a gas turbine. A methane-rich head product which advantageously can be utilized as such a fuel gas is produced by means of this embodiment of the invention wherein the liberated gaseous phase containing the light, driven off components and also the product gases, which are constituents in correspondence with the equilibrium with respect to the liquid phase, is subjected to a secondary scrubbing step to remove the product gases from the liberated gas phase. By the use of this process version, the recompression of the liberated gas fraction can then be dispensed with, or can at least be reduced, whereby the total economy of the process is enhanced.

In the secondary scrubbing step of the liberated gaseous fraction, a partial stream of the regenerated solvent is suitably employed. The secondary scrubbing step can be performed in a scrubbing column placed on top of the stripping column. By this arrangement, the partial stream of the solvent used during the secondary scrubbing can be regenerated together with the main solvent stream discharged from the stripping column. This represents an economically advantageous mode of operation. It is, of course, also possible to effect the secondary scrubbing step in a separate scrubbing column.

Suitable solvents in this connection are all organic, physically active solvents exhibiting selectivity for $C_{2+}$ and, respectively, $C_{3+}$ hydrocarbons. For example, solvents suitable for use in the present invention are cyclic hydrocarbons as described in the U.S. patent application Ser. No. 896 371.

After discharge from the bottom of the stripping column, the enriched solvent is sent to a regeneration step wherein $C_{2+}$ or $C_{3+}$ hydrocarbon products are removed from the solvent. Regeneration of the solvent can be performed by rectification or driving off the dissolved $C_{2+}$ hydrocarbons by means of partial evaporation. Therefore, the pressure is chosen in a way that it is possible to condensate the product at the head of the column at least partially for using as reflux.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein.

DETAILED DESCRIPTION OF DRAWINGS

Figure 1:
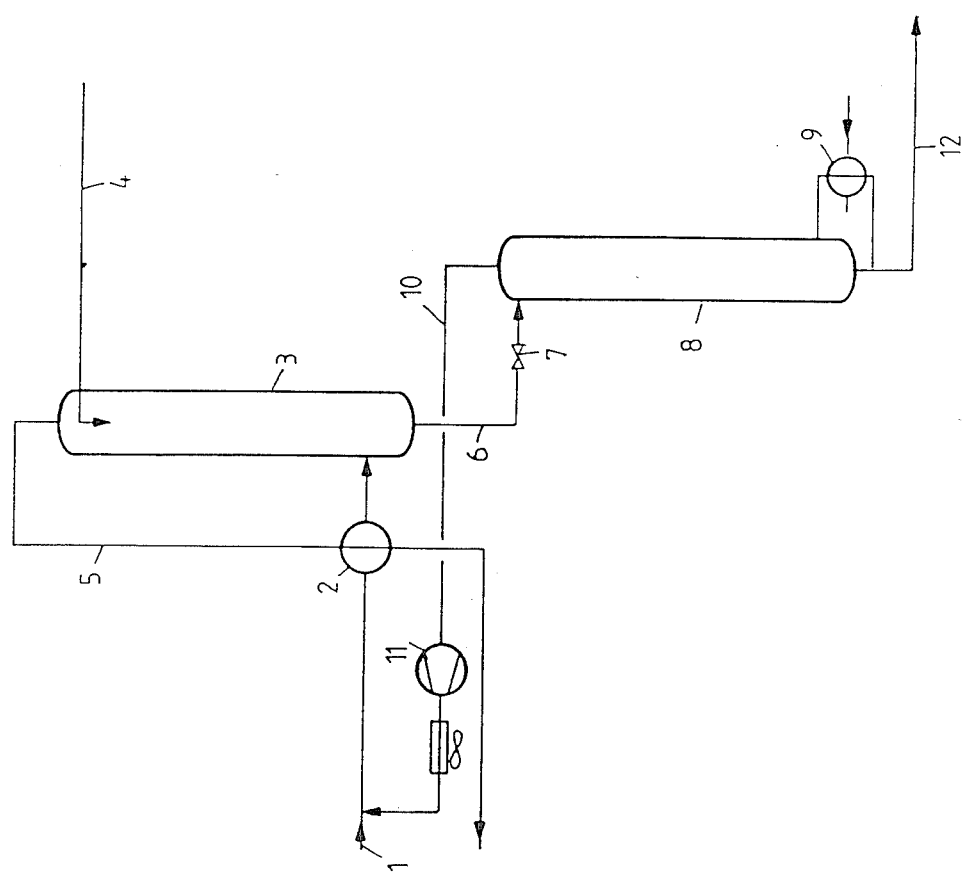
FIG. 1 is a schematic flowsheet of a preferred procedure with recycling of the liberated gaseous fraction to the scrubbing operation.

According to FIG. 1, a hydrocarbon-containing feedstream is introduced via conduit 1 under a pressure of 70 bar and, after cooling in a heat exchanger 2, fed into a scrubbing column 3 at the bottom thereof. In the scrubbing column 3, the $C_{2+}$ or $C_{3+}$ hydrocarbons are absorbed out of the feedstream by a countercurrently flowing regenerated solvent stream introduced via conduit 4, so that a fraction rich in methane is withdrawn overhead (conduit 5). This fraction is discharged after being heated in heat exchanger 2.

The solvent, loaded with the $C_{2+}$ and, respectively, $C_{3+}$ hydrocarbons is withdrawn from the bottom of scrubbing column 3 via conduit 6 and expanded, in a valve 7, to a pressure lying at least 5 bar below the critical pressure of the loaded scrubbing solvent. The solvent, brought to the lower pressure, is introduced into the upper section of a stripping column 8 equipped with a bottom heater or reboiler 9. The solvent is heated and partially vaporized in the stripping column 8 and a gaseous fraction is withdrawn via conduit 10 from the head of column 8. The gaseous fraction comprises essentially methane but also contains $C_{2+}$ or $C_{3+}$ hydrocarbons, in correspondence with the equilibrium to the liquid phase, and inerts. These inerts also contain so-called "flashgas", which is removed from the loaded solvent during expansion. This gaseous fraction is recompressed in a compressor 11 to the crude gas pressure and introduced into the crude gas upstream of the scrubbing operation. The solvent, reduced in its concentration of inert gases, is removed from the bottom of the stripping column 8 by way of conduit 12 and sent to a regeneration step, not shown.

Figure 2:
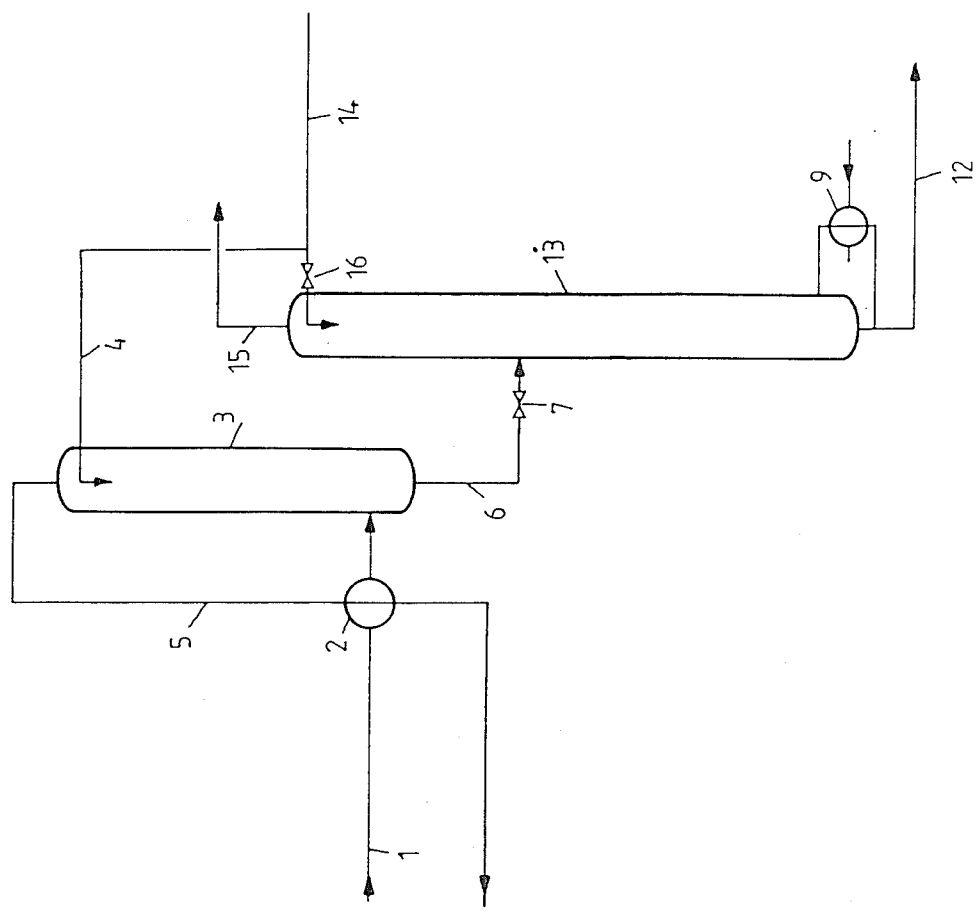
FIG. 2 is a schematic flowsheet of a preferred procedure with an additional scrubbing stage for the liberated gaseous fraction.

In the embodiment according to FIG. 2, identical parts have the same reference numerals as in FIG. 1. In the process illustrated in FIG. 2, the solvent, brought to a lower pressure by expansion, is fed to a column 13 likewise equipped with a reboiler 9. The solvent is likewise heated and partially vaporized. However, the liberated methane and inert gases are not recompressed and recycled into the scrubbing operation but rather are treated with regenerated solvent introduced via conduit 14. The $C_{2+}$ and, respectively $C_{3+}$ hydrocarbons, liberated with the methane and inert gases, are absorbed and a substantially pure methane fraction, is withdrawn overhead (conduit 15). This methane can be utilized as a fuel gas for a gas turbine.

The loaded solvent from this secondary scrubbing step is discharged via conduit 12, together with the solvent fed via conduit 6, and sent to a regeneration step, not illustrated. Moreover, a valve 16 is arranged in conduit 14 in order to expand the solvent in conduit 14, which had been brought to the pressure of column 3, to the pressure of column 13.

Without further elaboration, it is believed that one skilled in the art can, using the preceding description, utilize the present invention to its fullest extent. The following preferred specific numerical embodiments taken together with the drawings are, therefore, to be construed as merely illustrative, and not limitative of the remainder of the disclosure in any way whatsoever.

EXAMPLE 1

Obtaining $C_2H_{6+}$ from a natural gas under pressure (FIG. 1)
Amount of raw gas: 3,600 kmol/h
Pressure: 60 bar
Temperature: 303 K.
Composition:
  $CO_2$: 1 mol-%
  $CH_4$: 80.95 mol-%
  $C_2H_6$: 10.0 mol-%
  $C_3H_8$: 5.0 mol-%
  $i$-$C_4H_{10}$: 0.7 mol-%
  $n$-$C_4H_{10}$: 1.3 mol-%
  $i$-$C_5H_{10}$: 0.4 mol-%
  $n$-$C_5H_{10}$: 0.4 mol-%
  $C_{6+}$: 0.25 mol-%
Gas after $C_{2+}$ separation (conduit 5)
Amount: 2,996 kmol/h at 59 bar, 292 K.
Composition:
  $CO_2$: 0.69 mol-%
  $CH_4$: 97.20 mol-%
  $C_2H_6$: 2.105 mol-%
  $C_{3+}$: 0.005 mol-% (substantially scrubbing agent vapor)
Liquid after $C_{2+}$ separation (conduit 6)
Amount: 1730 kmol/h
Composition:
  $CO_2$: 2.2 mol%
  $CH_4$: 47.6 mol%
  $C_2H_6$: 31.0 mol%
  $C_{3+}$: 19.2 mol%

The loaded solvent after stripping (conduit 12) contains only the $C_{2+}$ product. Therefore, the loaded solvent discharged in conduit 12 contains product having the same amount and composition as that listed for the $C_{2+}$ product below.

$C_{2+}$ Product (after regeneration, not shown)
Amount: 604 kmol/h
Composition:
  $CO_2$: 2.56 mol-%
  $CH_4$: 0.38 mol-%
  $C_2H_6$: 49.14 mol-%
  $C_3H_8$: 29.77 mol-%
  $i$-$C_4$: 4.17 mol-%
  $n$-$C_4$: 7.74 mol-%
  $i$-$C_6$: 2.38 mol-%
  $n$-$C_5$: 2.38 mol-%
  $C_{6+}$: 1.48 mol-%
Regenerated Solvent (conduit 4)
Amount: 440 m³/h
Composition: $C_9$ aromate
Recycled material (conduit 10):
Amount: 1,125 kmol/h, pressure 20 bar.
Composition:
  $CO_2$: 2.1 mol%
  $CH_4$: 72.9 mol%
  $C_2H_6$: 21.3 mol%
  $C_{3+}$: 3.8 mol%
Compression energy for this compressor with $\eta = 0.7$:
N=1,190 KW
Solvent: $C_9H_{12}$
Amount of solvent 440 m³/h with T=278 K.

For the heater 9 of column 8, the regenerated solvent can be extensively utilized. The actually required amount of heat depends, therefore, on the type of regeneration.

The example has been set for a $C_2H_6$ scrubbing-out action of 82.5%. However, the yield can be further increased to a desired value by increasing the amount of solvent. The critical pressure of the loaded solvent in the bottom of the column 8 is 38 bar; consequently, the dissolved $C_1$ cannot be driven off under crude gas pressure. The loaded solvent is expanded to a pressure of 20 bar in expansion valve 7.

EXAMPLE 2

The head product driven off from the stripping column is not recycled but is discharged at a pressure of 20 bar after $C_{2+}$ rescrubbing (FIG. 2).

The amount of crude gas, crude gas pressure, crude gas temperature, and crude gas composition are as was in the first example.

|  | $CH_4$ Product (Conduit 5) | Intermediate Expansion Product $CH_4$ (Conduit 15) | $C_2H_6$ Product (After Regeneration) |
|---|---|---|---|
| $CO_2$ | 0.53 mol % | 1.12 mol % | 2.65 mol % |
| $CH_4$ | 97.78 mol % | 95.24 mol % | 0.46 mol % |
| $C_2H_6$ | 1.68 mol % | 3.63 mol % | 49.02 mol % |
| $C_3H_8$ | — | — | 29.73 mol % |
| $i$-$C_4$ | — | — | 4.16 mol % |
| $n$-$C_4$ | — | — | 7.73 mol % |
| $i$-$C_5$ | — | — | 2.38 mol % |
| $n$-$C_5$ | — | — | 2.38 mol % |
| $C_{6+}$ | 0.01 mol % | 0.01 mol % | 1.49 mol % |
| Amount (kmol/h) | 2,330.9 | 663.8 | 605.3 |
| Pressure (bar) | 59 | 20 | — |

| Loaded Solvent Before Expansion (conduit 6) | Loaded Solvent After Stripping (conduit 12) | Regenerated Solvent (conduit 14) |
|---|---|---|
| Amount: 1269.1 kmol/h | 605.4 kmol/h | 440 m³/h |

-continued

Composition:
| | | | |
|---|---|---|---|
| $CO_2$ | 1.9 mol % | 2.6 mol % | $C_9$ Aromate |
| $CH_4$ | 50.0 mol % | 0.5 mol % | (same amount and |
| $C_2H_6$ | 25.3 mol % | 49.0 mol % | composition as in |
| $C_3H_8$ | 22.8 mol % | 47.9 mol % | example 1, conduit 4) |

Type of solvent: $C_9H_{12}$
Solvent introduced into
 3: 333 m³/h (conduit 4)
 13: 214 m³/h (via valve 16)

Critical pressure of loaded solvent in bottom of column 8 is 38 bar.

The amount of solvent in total is higher than that used in example 1 with about the same yield of $C_2H_6$, but the recycle compressor is eliminated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for obtaining $C_{2+}$ or $C_{3+}$ hydrocarbons from gaseous mixtures that contain hydrocarbons and dissolved inert gases comprising: scrubbing the gaseous mixture with a physical liquid solvent selective for $C_{2+}$ or $C_{3+}$ hydrocarbons; expanding the enriched liquid solvent to an intermediate pressure below its critical pressure; stripping the expanded enriched liquid solvent by heating and partial evaporation to remove said dissolved inert gases; and subsequently regenerating the solvent.

2. A process according to claim 1, wherein the enriched solvent is expanded to a pressure at least 5 bar below the critical pressure of the enriched solvent.

3. A process according to claim 2, wherein expansion and stripping of the enriched solvent forms a gaseous fraction, which is subsequently compressed to the pressure of said gaseous mixture and recycled to the scrubbing step.

4. A process according to claim 2, wherein expansion and stripping of the enriched solvent forms a gaseous fraction which is subsequently subjected to a secondary scrubbing step for recovery of $C_{2+}$ or $C_{3+}$ hydrocarbons liberated from the solvent during expansion and stripping.

5. A process according to claim 4, wherein gas discharged from the secondary scrubbing stage is utilized as fuel gas.

6. A process according to claim 1, wherein expansion and stripping of the enriched solvent forms a gaseous fraction, which is subsequently compressed to the pressure of said gaseous mixture and recycled to the scrubbing step.

7. A process according to claim 1, wherein expansion and stripping of the enriched solvent forms a gaseous fraction which is subsequently subjected to a secondary scrubbing step for recovery of $C_{2+}$ or $C_{3+}$ hydrocarbons liberated from the solvent during expansion and stripping.

8. A process according to claim 7, wherein the secondary scrubbing step is conducted with a partial stream of regenerated solvent.

9. A process according to claim 8, wherein gas discharged from the secondary scrubbing stage is utilized as fuel gas.

10. A process according to claim 8, wherein the step of stripping the enriched solvent and the secondary scrubbing step are both performed in a single column, said stripping step being performed in a lower portion of the column and said secondary scrubbing step being performed in an upper portion of the column.

11. A process according to claim 10, wherein said partial stream or regenerated solvent is expanded to about the pressure of said column prior to delivery to said column.

12. A process according to claim 7, wherein gas discharged from the secondary scrubbing stage is utilized as fuel gas.

13. A process according to claim 7, wherein the step of stripping the enriched solvent and the secondary scrubbing step are both performed in a single column, said stripping step being performed in a lower portion of the column and said secondary scrubbing step being performed in an upper portion of the column.

* * * * *